US00PP33713P2

(12) United States Plant Patent
Probst

(10) Patent No.: US PP33,713 P2
(45) Date of Patent: Nov. 30, 2021

(54) ***COREOPSIS* PLANT NAMED 'FIREWHEEL'**

(50) Latin Name: ***Coreopsis* hybrid**
Varietal Denomination: Firewheel

(71) Applicant: Darrell Probst, Hubbardston, MA (US)

(72) Inventor: Darrell Probst, Hubbardston, MA (US)

( * ) Notice: Subject to any disclaimer, the term of this patent is extended or adjusted under 35 U.S.C. 154(b) by 0 days.

(21) Appl. No.: 17/317,005

(22) Filed: May 11, 2021

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of hybrid *Coreopsis* plant named 'Firewheel' that is characterized by its compact plant habit reaching an average of 50 cm in height and 70 cm in width, its floriferous and long blooming season of its sterile inflorescences that do not require deadheading; bloom commences in late-June and lasts until frost in Kensington, Conn., its large sized inflorescences with ray florets that are somewhat folded (not flat), ruffled, with serrated tips and are red-orange in color with yellow near the tips, its resistance to powdery mildew and leafspot, its cold hardiness at least to U.S.D.A. Zone 4, and its ease of propagation as cuttings can be taken throughout the growing season.

2 Drawing Sheets

Botanical classification: *Coreopsis* hybrid.
Variety denomination: 'Firewheel'.

BACKGROUND OF THE INVENTION

The present invention relates to a new and distinct cultivar of *Coreopsis* plant, botanically of hybrid origin and known as *Coreopsis* 'Firewheel' and will be referred to hereinafter by its cultivar name, 'Firewheel'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 4 in a wide range of flower colors and plant forms.

The Inventor made a controlled cross in August of 2015 in New Braintree, Mass. between an unnamed and unpatented proprietary plant from his breeding program as the female parent (ref. code N2 14-12) and pollen that was pooled from a variety of unnamed and unpatented proprietary plants from his breeding program as the male parent. The exact characteristics of the pollen parent are therefore unknown. 'Firewheel' was selected in September of 2016 as a single unique plant amongst the resulting seedlings.

Asexual propagation of the new cultivar was first accomplished by stem cuttings under the direction of the Inventor in Kensington, Conn. in September of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Firewheel' as a unique cultivar of *Coreopsis*.

1. 'Firewheel' exhibits a compact plant habit reaching an average of 50 cm in height and 70 cm in width.
2. 'Firewheel' exhibits a floriferous and long blooming season of its sterile inflorescences that do not require deadheading; bloom commences in late-June and lasts until frost in Kensington, Conn.
3. 'Firewheel' exhibits large sized inflorescences with ray florets that are somewhat folded (not flat), ruffled, with serrated tips and are red-orange in color with yellow near the tips.
4. 'Firewheel' exhibits resistance to powdery mildew and leafspot.
5. 'Firewheel' exhibits cold hardiness at least to U.S.D.A. Zone 4.
6. 'Firewheel' exhibits ease of propagation as cuttings can be taken throughout the growing season.

The female parent of 'Firewheel' differs from 'Firewheel' in having flowers that are pink in color and in being very fertile causing flower production to stop once seed has set. 'Firewheel' can be most closely compared to *Coreopsis* cultivars 'Daybreak' (U.S. Plant Pat. No. 27,138) and 'Darling Clementine' (U.S. Plant Pat. No. 31,843). 'Daybreak' is similar to 'Firewheel' in being resistant to powdery mildew and leaf spot, in having inflorescences with ray florets that are yellow in color with a red eye, and in having a long bloom season that does not require deadheading. 'Daybreak' differs from 'Firewheel' in having inflorescences with ray florets that are deeper golden yellow in color with a defined red eye, in being hardy to U.S.D.A. Zone 5, and in producing good cutting material only prior to onset of flowers versus all season. 'Darling Clementine' is similar to 'Firewheel' in having inflorescences with ray florets that are yellow and orange in color, in having a long bloom season that does not require deadheading, in being resistant to powdery mildew and leaf spot, and in being hardy to U.S.D.A. Zone 4. 'Darling Clementine' differs from 'Firewheel' in having inflorescences with ray florets that are relatively flat (not folded), are medium orange in color with much less ruffled and serrated tips.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to a listing on a website by Skagit Horticulture.

BRIEF DESCRIPTION OF THE DRAWINGS

The accompanying colored photographs illustrate the overall appearance and distinct characteristics of the new *Coreopsis*. The photographs were taken of a 4-month-old plant of 'Firewheel' as grown outdoors in one-gallon containers in Kensington, Conn.

The photograph in FIG. 1 provides a view of 'Firewheel' in bloom.

Figure 1:
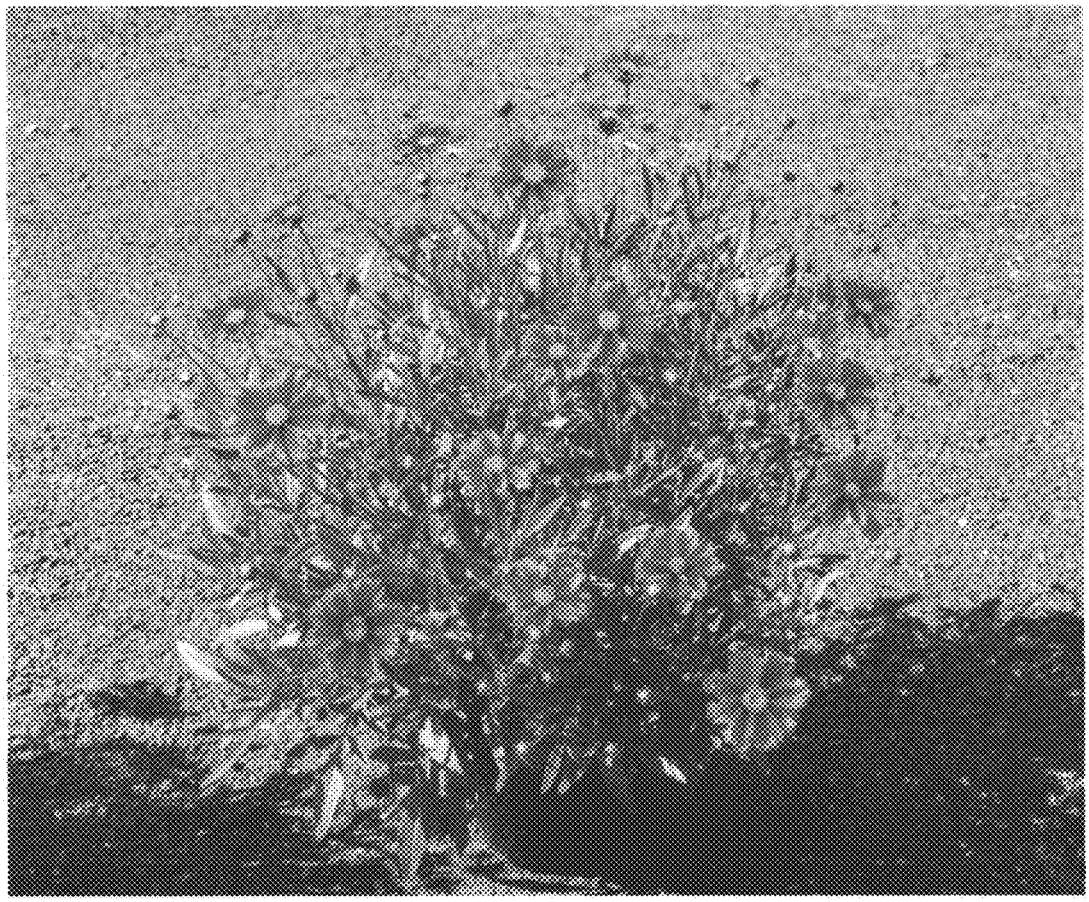
Figure 2:
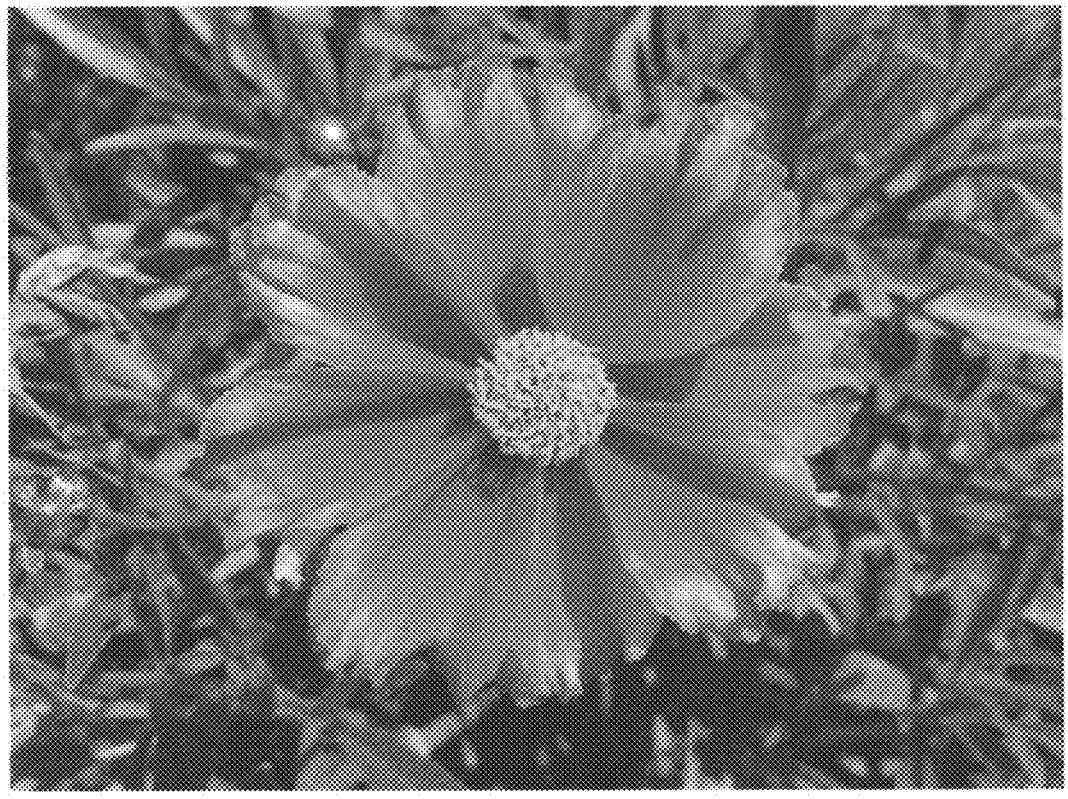

The photograph in FIG. 2 provides a close-up view of an inflorescence of 'Firewheel'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 4-month-old plants of 'Firewheel' as grown outdoors in one-gallon containers in Belchertown, Mass. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms from late-June until frost in Belchertown, Mass.

*Plant type.*—Herbaceous perennial.

*Plant habit.*—Clump-forming, compact, upright leafy flowering stems with inflorescences held above the foliage.

*Height and spread.*—An average of 48 cm in height (including inflorescences), 56 cm in width as grown in a one-gallon container.

*Cold hardiness.*—At least to U.S.D.A Zone 4.

*Diseases and pests.*—Resistance to powdery mildew (*Podosphaera macularis*) and leafspot (*Pseudomonas cichorii*). Resistance to pests has not been observed.

*Root description.*—Fibrous and fine, NN155A in color.

*Propagation.*—Stem cuttings.

*Time required for root initiation.*—An average of 10 days for root initiation.

*Growth rate.*—Vigorous, but stays compact.

Stem description:

*Shape.*—Triangular, solid.

*Stem color.*—144A.

*Stem strength.*—Strong.

*Stem size*—Main stems; an average of 10 cm in length and 8 mm in width, lateral stems; an average of 8 cm in length (excluding peduncles) and 5 mm in width.

*Stem surface.*—Glossy, moderately covered with villous hairs up to 2 mm in length, NN155C in color.

*Branching habit.*—Freely branched, an average of 18 basal main stems, lateral stems typically branched as oppositely arranaged pairs at each node.

*Internode length.*—An average of 5 cm.

Foliage description:

*Leaf division.*—Simple.

*Leaf margins.*—Entire, bi-fid and trifid.

*Leaf size.*—Entire leaves; an average of 8.5 cm in length and 5 cm in width, trifid leaves; center lobe an average of 6 cm in length and 1.5 cm in width, lateral lobes an average of 4.5 cm in length and in 5 mm width.

*Leaf shape.*—Linear.

*Leaf base.*—Cuneate.

*Leaf apex.*—Acute.

*Leaf venation.*—Pinnate, inconspicuous, same color as leaf.

*Leaf attachment.*—Sessile.

*Leaf arrangement.*—Opposite.

*Leaf surface.*—Upper and lower surfaces; dull and sparsely to moderately covered with villous hairs; up to 2 mm in length, NN155A in color.

*Leaf color.*—Young and mature upper surface; 137A, lower surface; 138B.

Flower description:

*Inflorescence type.*—Composite with a single row of ray florets surrounding disc florets in the center, forming a radiant head, inflorescences are borne on branch terminals in loose corymbs.

*Lastingness of inflorescence.*—8 to 10 days until senescence of ray florets, phyllaries and disc florets are persistent.

*Fragrance.*—Moderate floral scent.

*Quantity of inflorescences.*—Free flowering, an average of 12 corymbs per main branch, an average of 3 to 4 composits per corymb.

*Inflorescence size.*—Corymbs; up to 28 cm in length and 15 cm in width, composite; an average of 2 cm in depth and 6.5 cm in diameter.

*Inflorescence buds.*—Globose in shape, an average of 7 mm in depth and diameter, smooth and shiny surface; color; a blend of 152A and 153A.

*Peduncle.*—Rounded in shape, strong, an average of 19 cm in length and 1.5 mm in diameter, 144A in color, smooth and glabrous surface.

Phyllaries (involucral bracts):

*Phyllary number.*—2 rows; outer (lower) row 8, inner (upper) row 8.

*Phyllary arrangement.*—Outer (lower) phyllaries; unfused, slightly overlapping, held horizontal to upwards, inner (upper) phyllaries; surround receptacle with 50% of apical portion free.

*Phyllary size.*—Outer (lower) phyllaries; an average of 7 mm in length and 2 mm in width, inner (upper) phyllaries; an average of 9 mm in length and 5 mm in width.

*Phyllary color.*—Upper and lower surfaces, outer (lower) phyllaries; 144A, inner (upper) phyllaries; transluscent, 152B, margins flushed with 18A, base 144A.

*Phyllary texture.*—Outer (lower) phyllaries; glabrous and smooth on both surfaces, inner (upper) phyllaries; glabrous, slightly transluscent and slightly waxy on both surfaces.

*Phyllary apex.*—Acute.

*Phyllary base.*—Truncate.

*Phyllary shape.*—Outer (lower) phyllaries; elliptic to lanceolate, inner (upper) phyllaries; broadly lanceolate.

Ray florets (sterile):

*Number.*—8.

*Shape.*—Oblanceolate, with the appearance of 3 longitudinal sections, outer section sides curled inward.

*Size.*—An average of 2.4 cm in length and 2 cm in width.

*Apex.*—Rounded with serrated and undulate (ruffled) lobes.

*Base.*—Cuneate.

*Margins.*—Entire and slightly undulate.

*Aspect.*—Held mainly horizontal and slightly upwards, perpendicular to peduncle.

*Texture.*—Upper surface; satiny, velvety, glabrous and dull, lower surface; glabrous with a slight sheen.

*Color.*—Upper surface when opening; 13A, flushed with 34A at the base, lower surface when opening; 11A; upper surface when fully open; N34A, flushed with 13A at the tips, fully open lower surface; 12A and 12B.

Disc florets (male and female):

*Number.*—An average of 60.

*Shape.*—Tubular, corolla is fused, flared and slightly curled at apex.

*Size.*—About 5.5 mm in length and 1 mm in width.

*Color.*—En masse; 21A, individual; corolla (tube) base and mid-section transluscent, 11A in color.

*Receptacle.*—An average of 8 mm in diameter and 5 mm in depth, 144A in color.

Reproductive organs:

*Presence.*—Disc florets only.

*Gynoecium.*—1 Pistil; an average of 7 mm in length, style; very fine and 11B in color, bifid pillose, stigma; 17A in color with recurved branches about 0.5 mm in length, ovary is inferior, oblong in shape, an average of 2 mm in length and 1 mm in width, and 145A in color.

*Androecium.*—4 stamens, fused into tube surrounding style, an average of 4 mm in length and less than 0.5 mm in width, 200B in color, pollen; abundant in quantity and 17B in color.

*Seed.*—Seed development has not been observed.

It is claimed:

1. A new and distinct cultivar of *Coreopsis* plant named 'Firewheel' as herein illustrated and described.

* * * * *